United States Patent
Langbein et al.

[11] 3,933,832
[45] Jan. 20, 1976

[54] N-(1-(ω-PHENYL-ALKYL)-PIPERIDYL-4)-N-(α-PYRIDYL)-CARBOXYLIC ACID AMIDES AND SALTS THEREOF

[75] Inventors: Adolf Langbein; Herbert Merz, both of Ingelheim am Rhein; Gerhard Walther; Klaus Stockhaus, both of Bingen (Rhine), all of Germany

[73] Assignee: Boehringer Ingelheim GmbH, Ingelheim am Rhein, Germany

[22] Filed: Aug. 14, 1974

[21] Appl. No.: 497,455

[30] Foreign Application Priority Data
Aug. 20, 1973 Germany............................ 2341965

[52] U.S. Cl............................. 260/293.69; 424/267
[51] Int. Cl.[2]..................................... C07D 211/58
[58] Field of Search................................ 260/293.69

[56] References Cited
UNITED STATES PATENTS

| | | | |
|---|---|---|---|
| 3,141,823 | 7/1964 | Janssen et al. | 260/293.77 |
| 3,163,654 | 12/1964 | Hiltmann et al. | 260/293.69 |
| 3,164,600 | 1/1965 | Janssen | 260/293.69 |
| 3,594,477 | 7/1971 | Wollweber et al. | 260/293.69 |

OTHER PUBLICATIONS
Burger, *Medicinal Chemistry*, 3rd ed., Part I, Wiley – Interscience (1970), p. 76.

*Primary Examiner*—Sherman D. Winters
*Attorney, Agent, or Firm*—Hammond & Littell

[57] ABSTRACT

Compounds of the formula

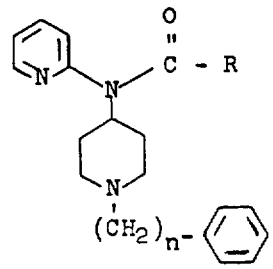

wherein
R is straight or branched alkyl of 1 to 3 carbon atoms, alkoxy of 1 to 2 carbon atoms or phenyl, and
n is an integer from 2 to 4, inclusive,
and non-toxic, pharmacologically acceptable acid addition salts thereof; the compounds as well as the salts are useful as non-narcotic analgesics.

3 Claims, No Drawings

N-(1-(ω-PHENYL-ALKYL)-PIPERIDYL-4)-N-(α PYRIDYL)-CARBOXYLIC ACID AMIDES AND SALTS THEREOF

This invention relates to novel N-[1-(ω-phenylalkyl)-piperidyl-4]-N-(α-pyridyl)-carboxylic acid amides and non-toxic acid addition salts thereof, as well as to methods of preparing these compounds.

BACKGROUND OF THE INVENTION

A class of 4-phenylamino-piperidines with strong analgesic activity is disclosed in French Pat. No. M 2430 (C.A. 62, 14634), and U.S. Pat. No. 3,141,823 discloses an analgesic and tranquilizing composition containing one particular compound of that class, namely N-(1-phenethyl-4-piperidyl)-propionanilide (generic name: Fentanyl), in combination with droperidol. However, fentanyl, being a very strong morphine-like analgesic, has a very substantial addiction potential.

OBJECTS OF THE INVENTION

It is an object of the present invention to provide a new class of N-piperidyl-N-pyridyl-carboxamides.

It is another object of the present invention to provide a novel class of compounds having strong analgesic properties, but no addiction potential.

Other objects and advantages of the invention will become apparent as the description thereof proceeds.

THE INVENTION

The above objects are achieved by providing a novel class of N-piperidyl-N-pyridyl-carboxamides represented by the formula

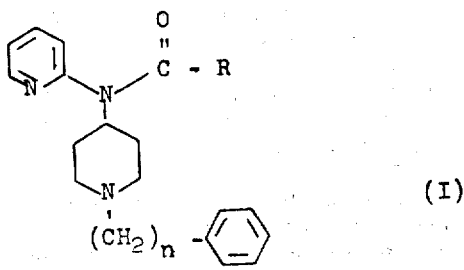

(I)

wherein
R is straight or branched alkyl of 1 to 3 carbon atoms, alkoxy of 1 to 2 carbon atoms or phenyl, and
n is an integer from 2 to 4, inclusive, and non-toxic, pharmacologically acceptable acid addition salts thereof.

The compounds embraced by formula I above may be prepared by the following methods:

Method A

Acylation of a 1-phenylalkyl-4-[N-(α-pyridyl)-amino]-piperidine of the formula

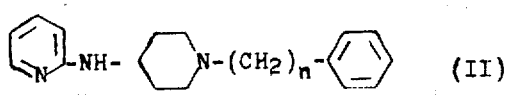

(II)

wherein
n has the meanings defined above, with an acylacting agent of the formula

(III)

wherein
R has the same meanings as in formula I, and X is halogen or R—COO—, where R has the meanings previously defined.

The reaction is advantageously performed in a non-hydrolizing, organic solvent, and preferably in the presence of an acidbinding agent. The reaction temperature is variable within wide limits, namely between room temperature and the boiling point of the reaction mixture.

Method B

Reaction of a piperidyl-(4)-N-(α-pyridyl)-carboxylic acid amide of the formula

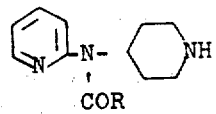

(IV)

wherein R has the same meanings as in formula I, with an alkylating agent of the formula

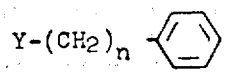

(V)

wherein
n has the meanings previously defined, and
Y is halogen, arylsulfonyloxy or alkylsulfonyloxy.

The alkylation is effected with the calculated quantity or a slight excess of the alkylating agent. It is advantageous to alkylate in the presence of an acid-binding agent and an inert solvent or mixture of solvents. The reaction temperature is variable within wide limits; temperatures between 0°C and the boiling point of the solvent or mixture of solvents are preferred.

The starting compounds of the formula II are prepared by reacting α-chloro-pyridine with 4-amino-1-benzylpiperidine in the presence of copper powder to form 4-[N-(αpyridyl)-amino]-1-benzyl-piperidine of the formula

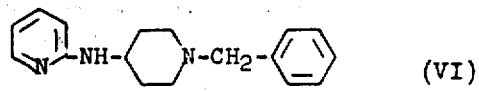

(VI)

debenzylating the compound of the formula VI, and subsequently alkylating the debenzylation product.

Compounds of the formula IV are obtained, starting from a compound of the formula VI, by acylation and subsequent debenzylation.

The compounds embraced by formula I are organic bases and therefore form acid addition salts with inorganic or organic acids. Examples of non-toxic, pharmacologically acceptable acid addition salts are those formed with hydrochloric acid, hydrobromic acid, hydroiodic acid, hydrofluoric acid, sulfuric acid, phosphoric acid, nitric acid, acetic acid, propionic acid, butyric acid, valeric acid, pivalic acid, caproic acid, capric acid, oxalic acid, malonic acid, succinic acid, maleic acid, fumaric acid, lactic acid, citric acid, malic acid, benzoic acid, phthalic acid, cinnamic acid, salicylic acid, p-hydroxybenzoic acid, ascorbic acid, 8-chlorotheophilline, methanesulfonic acid, ethanephosphonic acid or the like.

The following examples illustrate the present invention and will enable others skilled in the art to understand it more completely. It should be understood, however, that the invention is not limited solely to the particular examples given below.

Preparation of starting compounds:

EXAMPLE A

4-[N-(α-Pyridyl)-amino]-1-phenethyl-piperidine a. 4-[N-(α-pyridyl-amino]-1-benzyl-piperidine A mixture consisting of 79.2 gm (0.7 mol) of 2-chloro-pyridine, 380.4 gm (2 mols) of 4-amino-1-benzyl-piperidine and 45.9 gm (0.75 gm-atom) of copper powder was stirred for 20 hours at an internal temperature of 180°C. Thereafter, the reaction mixture was allowed to cool, the dark oil was dissolved in 750 ml of 6 N hydrochloric acid, the resulting solution was admixed with 50 gm of activated charcoal, and the mixture was briefly heated and then vacuum-filtered through 20 gm of diatomaceous earth while hot. The filtrate was cooled and then adjusted to pH 4.5–5.0 with aqueous 30% sodium hydroxide, and this solution (phase 1) was extracted three times with 100 ml of methylene chloride each (phase 2). The aqueous phase 1 was now adjusted to pH 8 with aqueous 30% sodium hydroxide and then extracted four times with 150 ml of ether each (phase 3). The ethereal phase 3 was extracted twice with water, dried and evaporated; the two aqueous extracts were combined (phase 4) and set aside for recovery of the 4-amino-1-benzyl-piperidine starting compound. The evaporation of the ethereal phase 3 left as a residue 127 gm of raw reaction product having a melting point of 90°–100°C, which was recrystallized once from petroleum ether (b.p. 80°–110°C), yielding 78.3 gm (55.7% of theory) of 4-[N-(α-pyridyl)-amino]-1-benzyl-pyridine, m.p. 106°–107°C.

Recovery of starting compounds

The methylene chloride extracts (phase 2) were washed with water, dried and evaporated, leaving 20 gm of 2-chloro-pyridine.

The combined aqueous extracts (phase 4) were saturated with caustic soda, whereupon most of the unreacted, oily 4-amino-1-benzyl-piperidine contained therein precipitated out and was separated. The aqueous mother liquor was once again extracted with methylene chloride, the organic extract was combined with the 4-amino-1-benzyl-piperidine already recovered, the methylene chloride was evaporated, and the residue was distilled in a high vacuum over solid potassium hydroxide. Thus a total of 228 gm of 4-amino-1-benzyl-piperidine, b.p. 96°–100°C at 0.2 mm Hg, were recovered, which corresponded to about 60% of the amount originally used.

b. 4-[N-(α-pyridyl)-amino]-piperidine and its hydrochloride

A solution of 26.7 gm (0.1 mol) of 4-[N-(α-pyridyl)-amino[-1-benzyl-piperidine in 500 ml of ethanol was admixed with 5 gm of palladized (10%) charcoal, and the mixture was hydrogenated at 60°C and 5 atmospheres pressure until the calculated amount of hydrogen for debenzylation had been absorbed. Thereafter, the catalyst was vacuum-filtered off, the filtrate was evaporated, and the residue was recrystallized from ethyl acetate, yielding 19.5 gm (91% of theory) of 4-[N-(α-pyridyl)-amino]-piperidine, m.p. 158°–161°C.

c. A mixture consisting of 1.77 gm (0.01 mol) of 4-[N-(α-pyridyl)-amino]-piperidine, 2.04 gm (0.011 mol) of 2-phenethyl bromide, 1.26 gm (0.015 mol) of sodium bicarbonate and 25 ml of a mixture of tetrahydrofuran and dimethylformamide (3:1) was refluxed for five hours. After cooling, the solvent mixture was evaporated, and the residue was extracted several times with chloroform. The combined chloroform extracts were extracted five times with water, dried and evaporated, the residual oil was dissolved in 20 ml of ethanol, the solution was acidified with 2 ml of 5 N ethanolic hydrochloric acid, and ether was added until crystallization commenced. 2.3 gm (72.3% of theory) of 4-[N-(α-pyridyl)-amino]-1-phenethyl-piperidine hydrochloride, m.p. 223°–225°C, crystallized out.

EXAMPLE B

4-[N-(α-pyridyl)-N-propionyl-amino]-piperidine hydrochloride a. 4-[N-(α-pyridyl)-N-propionyl-amino]-1-benzyl-piperidine A mixture consisting of 2.67 gm (0.01 mol) of 4-[N-(α-pyridyl)-amino]-1-benzyl-piperidine and 6 gm of propionic acid anhydride was refluxed for 90 minutes. Thereafter, the excess, unreacted anhydride was evaporated in vacuo, and the residue was poured into a mixture of 100 gm of ice and 20 ml of concentrated ammonia. The resulting aqueous suspension was extracted three times with 100 ml of methylene chloride each, the combined organic extracts were dried over sodium sulfate and then evaporated, and the residue was recrystallized from ethanol. 2.8 gm of 4-[N-(α-pyridyl)-N-propionylamino]-1-benzyl-piperidine, m.p. 90°–93°C, were obtained.

b. 3.23 gm (0.01 mol) of 4-[N-(α-pyridyl)-N-propionylamino]-1-benzyl-piperidine were converted in conventional manner into the monohydrochloride, which was then dissolved in 50 ml of ethanol. After addition of 5 gm of palladized charcoal the mixture was hydrogenated at 20°C and 5 atmospheres pressure until the calculated amount of hydrogen for debenzylation had been absorbed. Thereafter, the catalyst was removed by vacuum filtration, the filtrate was evaporated, and the residue was recrystallized from ethanol/ether. 2.56 gm (95 % of theory) of 4-[N-(α-pyridyl)-N-propionyl-amino]-piperidine hydrochloride, m.p. 221°–222°C, were obtained. Preparation of end products of the formula I:

EXAMPLE 1

4-[N-(α-Pyridyl)-N-(ethoxycarbonyl)-amino]-1-phenethylpiperidine and its hydrochloride by method A A mixture consisting of 2.81 gm (0.01 mol) of 4-[N-(α-pyridyl)-amino]-1-phenethyl-piperidine, 15 ml of chloroform, 2 ml of pyridine and 5.36 gm (0.05 mol) of ethyl chloroformate was refluxed for 24 hours. Thereafter, the reaction solution was allowed to cool and was then poured over 500 gm of ice while adding 50 ml of concentrated ammonia thereto. The resulting aqueous mixture was then extracted five times with 50 ml of chloroform each, the combined organic extracts were washed with water, dried over sodium sulfate and vacuum-filtered, and the solvent was evaporated from the filtrate. The oily residue, 4-[N-(α-pyridyl)-N-(ethoxycarbonyl)-amino]-1-phenethyl-piperidine, was dissolved in 20 ml of ethanol, the solution was made weakly acid with 2 ml of 5 N ethanolic hydrochloric acid, then ether was carefully added until precipitation commenced, and the precipitate was collected. 2.5 gm (64.2% of theory) of the hydrochloride, m.p. 183°–186°C, of the formula

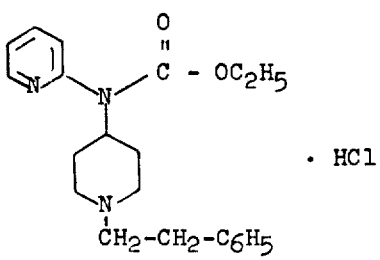

were obtained.

EXAMPLE 2

4-[N-(α-Pyridyl)-N-propionyl-amino]-1-phenethyl-piperidine and its hydrochloride by method B A mixture consisting of 2.69 (0.01 mol) of 4-[N-(α-pyridyl)-N-propionyl-amino]-piperidine hydrochloride, 2.4 gm (0.011 mol) of 2-phenethyl bromide, 2.52 gm (0.03 mol) of sodium bicarbonate and 25 ml of a mixture of tetrahydrofuran and dimethylformamide (3:1) was refluxed for four hours. Thereafter, 100 ml of methylene chloride were added to the reaction mixture, and the resulting suspension was extracted five times with 100 ml of water each. The organic phase was dried over sodium sulfate, the solvent was evaporated, and the oily residue, 4-[N-(α-pyridyl)-N-propionyl-amino]-1-phenethyl-piperidine, was dissolved in 20 ml of ethanol. The resulting solution was made weakly acid with 2 ml of 5 N ethanolic hydrochloric acid, and then ether was added until crystallization commenced. The crystalline product was collected, yielding 1.95 gm (52% of theory) of the hydrochloride, m.p. 217°–221°C, of the formula

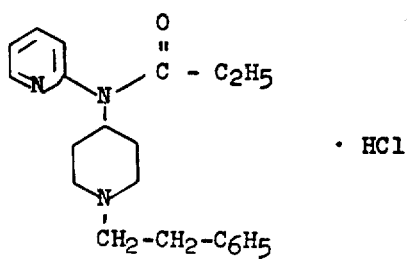

EXAMPLE 3

Using a procedure analogous to that described in Example 2, 57% of theory of 4-[N-(α-pyridyl)-N-acetyl-amino]-1-phenethyl-piperidine, m.p. 83°–84°C, of the formula

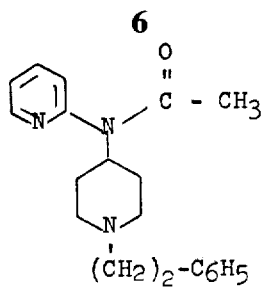

was obtained from 4-[N-(α-pyridyl)-N-acetyl-amino]-piperidine and 2-phenethyl bromide.

EXAMPLE 4

Using a procedure analogous to that described in Example 2, 62% of theory of 4-[N-(α-pyridyl)-N-(n-butyryl)-amino]-1-phenethyl-piperidine and its hydrochloride, m.p. 208°–209°C, of the formula

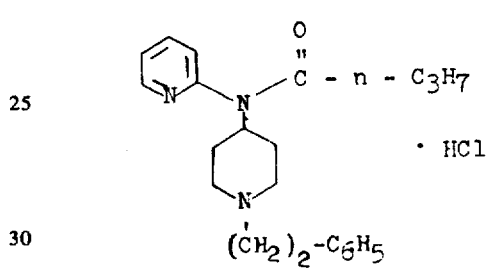

was obtained from 4-[N-(α-pyridyl)-N-(n-butyryl)-amino]-piperidine and 2-phenethyl bromide.

EXAMPLE 5

Using a procedure analogous to that described in Example 2, 53% of theory of 4-[N-(α-pyridyl)-N-isobutyrylamino]-1-phenethyl-piperidine and its hydrochloride, m.p. 219°–220°C, of the formula

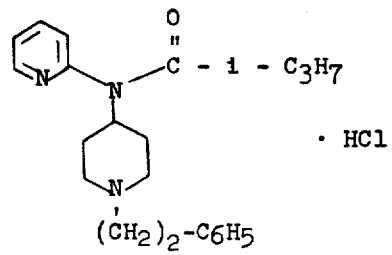

was obtained from 4-[N-(α-pyridyl)-N-isobutyryl-amino]-piperidine and 2-phenethyl bromide.

EXAMPLE 6

Using a procedure analogous to that described in Example 2, 67% of theory of 4-[N-(α-pyridyl)-N-benzoyl-amino]-1-phenethyl-piperidine and its hydrochloride, m.p. 235°–240°C, of the formula

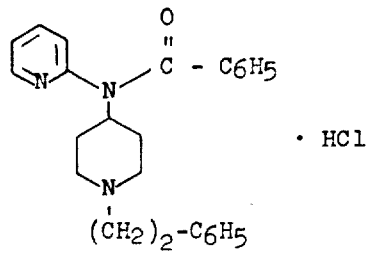

was obtained from 4-[N-(α-pyridyl)-N-benzoyl-amino]-piperidine and 2-phenethyl bromide.

EXAMPLE 7

Using a procedure analogous to that described in Example 1, 24% of theory of 4-[N-(α-pyridyl)-N-(propionyl-amino]-1-(γ-phenyl-n-propyl)-piperidine and its hydrochloride, m.p. 119°–124°C, of the formula

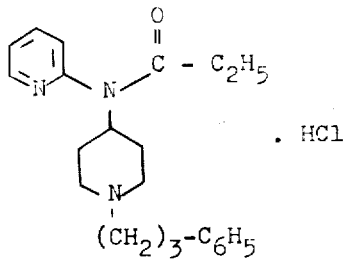

was obtained from 4-[N-(α-pyridyl)-amino]-1-(γ-phenyl-n-propyl)-piperidine and propionyl chloride.

EXAMPLE 8

Using a procedure analogous to that described in Example 1, 32% of theroy of 4-[N-(α-pyridyl)-N-(propionyl)amino]-1-(4'-phenyl-n-butyl)-piperidine and its hydrochloride, m.p. 189°–191°C, of the formula

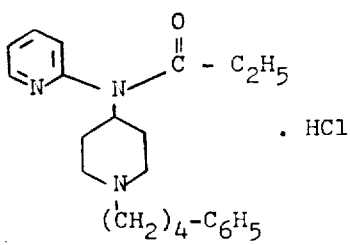

was obtained from 4-[N-(α-pyridyl)-amino]-1-(4'-phenyl-n-butyl)-piperidine and propionyl chloride.

The compounds of the present invention, that is, those embraced by formula I above and their non-toxic, pharmacologically acceptable acid addition salts, have useful pharmacodynamic properties; more particularly, they exhibit strong analgesic activity in warm-blooded animals, such as mice and rats, with practically no morphine-like side efects, such as respiration depression, Straub's tail or the like.

For pharmaceutical purposes the compounds according to the present invention are administered to warm-blooded animals enterally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. The effective oral dosage unit range of the compounds according to the present invention is from 0.16 to 5.0 mgm/kg body weight, preferably 0.83 to 2.5 mgm/kg body weight; the parenteral dosage unit range is about 0.5 to 1.67 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 9

Tablets

The tablet composition is compounded from the following ingredients:

| | |
|---|---|
| 4-[N-(α-pyridyl)-N-ethoxycarbonyl)-amino]-1-phenethyl-piperidine hydrochloride | 50.0 parts |
| Lactose | 95.0 parts |
| Corn starch | 45.0 parts |
| Colloidal silicic acid | 2.0 parts |
| Soluble starch | 5.0 parts |
| Magnesium stearate | 3.0 parts |
| Total | 200.0 parts |

Preparation

The active ingredient is admixed with part of the excipients, and the mixture is granulated with a solution of the soluble starch in water. After drying of the granulate, the remaining excipients are admixed with it, and the mixture is compressed into 200 ngn-tablets. Each tablet contains 50 mgm of the piperidine compound and is an oral dosage unit with very effective analgesic action.

EXAMPLE 10

Coated pills

The pill core composition is compounded from the following ingredients:

| | |
|---|---|
| 4-[N-(α-pyridyl)-N-(propionyl)-amino]-1-phenethyl-piperidine hydrochloride | 75.0 parts |
| Lactose | 100.0 parts |
| Corn starch | 65.0 parts |
| Colloidal silicic acid | 2.0 parts |
| Soluble starch | 5.0 parts |
| Magnesium stearate | 3.0 parts |
| Total | 250.0 parts |

Preparation

The ingredients are compounded as described in Example 9, and the composition is compressed into 250 mgmpill cores which are subsequently coated in conventional manner with a thin shell consisting essentially of a mixture of sugar, talcum and gum arabic. Each coated pill contains 75 mgm of the piperidine compound and is an oral dosage unit composition with very effective analgesic action.

EXAMPLE 11

Suppositories

The suppository composition is compounded from the following ingredients:

| | |
|---|---|
| 4-[N-(α-pyridyl)-N-(ethoxycarbonyl)-amino]-1-phenethyl-piperidine hydrochloride | 50.0 parts |
| Lactose | 250.0 parts |
| Suppository base (e.g. cocoa butter) | 1400.0 parts |
| Total | 1700.0 parts |

Preparation

The active ingredient and the lactose are intimately admixed with each other, and the mixture is homogeneously blended in the molten suppository base. 1700 mgm-portions of the composition are poured into cooled suppository molds and allowed to harden therein. Each suppository contains 50 mgm of the piperidine compound and is a rectal dosage unit composition with very effective analgesic action.

Analogous results are obtained when any one of the other compounds embraced by formula 1 or a nontoxic, pharmacologically acceptable acid addition salt thereof is substituted for the particular piperidine compound in Examples 9 through 11. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

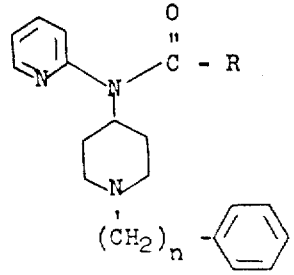

wherein
R is alkyl of 1 to 3 carbon atoms, alkoxy of 1 to 2 carbon atoms or phenyl, and
$n$ is an integer from 2 to 4, inclusive,
or a non-toxic, pharmacologically acceptable acid addition salt thereof.

2. A compound of claim 1, which is 4-[N-($\alpha$-pyridyl)-N-(ethoxycarbonyl)-amino]-1-phenethyl-piperidine or a nontoxic, pharmacologically acceptable acid addition salt thereof.

3. A compound of claim 1, which is 4-[N-($\alpha$-pyridyl)-N-propionyl-amino]-1-phenethyl-piperidine or a nontoxic, pharmacologically acceptable acid addition salt thereof.

* * * * *